(12) United States Patent
Furukawa

(10) Patent No.: US 10,851,802 B2
(45) Date of Patent: Dec. 1, 2020

(54) METHOD OF MANUFACTURING CENTRIFUGAL PUMP

(71) Applicant: TERUMO KABUSHIKI KAISHA, Tokyo (JP)

(72) Inventor: Shinpei Furukawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 731 days.

(21) Appl. No.: 15/422,830

(22) Filed: Feb. 2, 2017

(65) Prior Publication Data

US 2017/0146030 A1    May 25, 2017

Related U.S. Application Data

(63) Continuation of application No. PCT/JP2015/073557, filed on Aug. 21, 2015.

(30) Foreign Application Priority Data

Sep. 24, 2014    (JP) .................. 2014-194328

(51) Int. Cl.
- *F04D 29/62*   (2006.01)
- *F04D 29/42*   (2006.01)

(Continued)

(52) U.S. Cl.
CPC ......... *F04D 29/628* (2013.01); *A61M 1/1012* (2014.02); *A61M 1/1013* (2014.02);
(Continued)

(58) Field of Classification Search
None
See application file for complete search history.

(56) References Cited

U.S. PATENT DOCUMENTS

| | | | |
|---|---|---|---|
| 5,360,317 A | | 11/1994 | Clausen et al. |
| 5,458,459 A | * | 10/1995 | Hubbard ............. F04D 29/0413 415/206 |

(Continued)

FOREIGN PATENT DOCUMENTS

| | | |
|---|---|---|
| JP | 2007089973 A | 4/2007 |
| JP | 2007222670 A | 9/2007 |

(Continued)

OTHER PUBLICATIONS

JPO Office Action dated May 24, 2017 for 2016-550041.

*Primary Examiner* — Kenneth J Hansen
*Assistant Examiner* — Jason Fountain
(74) *Attorney, Agent, or Firm* — MacMillan, Sobanski & Todd, LLC

(57) ABSTRACT

A centrifugal blood pump prevents a shaft member from oscillating due to expansion of a pump housing resulting from pressurization of the blood. The centrifugal blood pump is manufactured by assembling a bottom member 21 and a lid member 22, and compressing them in a direction in which the bottom member 21 and the lid member 22 approach each other by a deformation amount along their outer circumferential walls. The lid member and the bottom member are joined while in the compressed state in order to create a preloading force between the shaft member and bearings to resist the expansion due to pressurization of the blood during use.

8 Claims, 4 Drawing Sheets

(51) Int. Cl.

| | | |
|---|---|---|
| *A61M 1/10* | (2006.01) | |
| *F04D 29/02* | (2006.01) | |
| *B29C 65/00* | (2006.01) | |
| *B23K 37/04* | (2006.01) | |
| *B29C 65/16* | (2006.01) | |
| *B29C 65/78* | (2006.01) | |
| *B23K 26/08* | (2014.01) | |
| *B23K 26/324* | (2014.01) | |
| *B23K 26/282* | (2014.01) | |
| *F04D 29/041* | (2006.01) | |
| *B23K 26/21* | (2014.01) | |
| *B23K 26/18* | (2006.01) | |
| *F04D 7/04* | (2006.01) | |
| *F04D 29/046* | (2006.01) | |
| *B29L 31/00* | (2006.01) | |
| *A61M 1/12* | (2006.01) | |
| *B23K 103/00* | (2006.01) | |
| *F04D 13/02* | (2006.01) | |

(52) U.S. Cl.
CPC ....... *A61M 1/1029* (2014.02); *B23K 26/0823* (2013.01); *B23K 26/18* (2013.01); *B23K 26/21* (2015.10); *B23K 26/282* (2015.10); *B23K 26/324* (2013.01); *B23K 37/0435* (2013.01); *B29C 65/1635* (2013.01); *B29C 65/1658* (2013.01); *B29C 65/1683* (2013.01); *B29C 65/7841* (2013.01); *B29C 66/1286* (2013.01); *B29C 66/12841* (2013.01); *B29C 66/543* (2013.01); *B29C 66/65* (2013.01); *B29C 66/73921* (2013.01); *B29C 66/8322* (2013.01); *F04D 7/04* (2013.01); *F04D 29/026* (2013.01); *F04D 29/041* (2013.01); *F04D 29/046* (2013.01); *F04D 29/426* (2013.01); *A61M 1/10* (2013.01); *A61M 1/101* (2013.01); *A61M 1/1036* (2014.02); *A61M 1/122* (2014.02); *A61M 2207/00* (2013.01); *B23K 2103/42* (2018.08); *B29C 65/1616* (2013.01); *B29C 66/71* (2013.01); *B29C 66/73115* (2013.01); *B29L 2031/7496* (2013.01); *B29L 2031/753* (2013.01); *F04D 13/024* (2013.01); *F05D 2230/234* (2013.01)

(56) References Cited

U.S. PATENT DOCUMENTS

| | | | |
|---|---|---|---|
| 5,575,630 | A | 11/1996 | Nakazawa et al. |
| 5,588,812 | A * | 12/1996 | Taylor ................. F04D 13/0646 415/900 |
| 6,690,708 | B2 * | 2/2004 | Ishimaru .............. G02B 6/4208 372/108 |
| 6,929,777 | B1 * | 8/2005 | Litwak ................ A61M 1/0076 261/DIG. 28 |
| 9,429,160 | B2 * | 8/2016 | Tanaka ...................... F04D 1/00 |
| 10,260,528 | B2 * | 4/2019 | Itamochi .............. A61M 1/1698 |
| 10,294,944 | B2 * | 5/2019 | Aber ...................... F04D 13/06 |
| 2010/0065200 | A1 * | 3/2010 | Sarver .................. C07D 471/06 156/272.8 |
| 2013/0251516 | A1 | 9/2013 | Tanaka et al. |
| 2014/0255225 | A1 * | 9/2014 | Aber ...................... F04D 13/06 417/420 |
| 2016/0281743 | A1 | 9/2016 | Itamochi |

FOREIGN PATENT DOCUMENTS

| | | |
|---|---|---|
| JP | 4548450 B2 | 7/2010 |
| JP | 2013053591 A | 3/2013 |
| WO | 9509984 | 4/1995 |
| WO | 2014109029 A | 7/2014 |

* cited by examiner

METHOD OF MANUFACTURING CENTRIFUGAL PUMP

CROSS REFERENCE TO RELATED APPLICATIONS

This application is a continuation of PCT Application No. PCT/JP2015/073557, filed Aug. 21, 2015, based on and claiming priority to Japanese application no. 2014-194328, filed Sep. 24, 2014, both of which are incorporated herein by reference in their entirety.

BACKGROUND OF THE INVENTION

The present invention relates to a method of manufacturing a centrifugal pump.

In the related art, as blood pumps which transport blood, there have been known turbo-type pumps which send out blood in response to centrifugal force. The turbo-type pump includes a hollow housing, an impeller that is rotatably accommodated in the housing, a rotary shaft (i.e., shaft member) that serves as a rotation center of the impeller, an upper bearing that rotatably supports an upper end portion of the rotary shaft, and a lower bearing that rotatably supports a lower end portion of the rotary shaft (see, e.g., Japanese Patent No. 4548450).

In the blood pump disclosed in Japanese Patent No. 4548450, the upper bearing has a tubular shape. The upper end portion of the rotary shaft has an outer diameter slightly smaller than the inner diameter of the upper bearing and is inserted therein. Accordingly, an inner peripheral portion of the upper bearing and an outer peripheral portion of the upper end portion of the rotary shaft are in a surface contacting state. In addition, the lower bearing also has a tubular shape, and the lower end portion of the rotary shaft has an outer diameter slightly smaller than the lower bearing inner diameter and is inserted into the lower bearing.

However, in the blood pump disclosed in Japanese Patent No. 4548450, when the impeller rotates, the internal pressure of blood contained within the housing rises and the housing expands outward (especially including expansion in the axial direction of the rotary shaft). In this case, a separation distance between the upper and lower bearings increases by an amount determined by expansion of the housing. Consequently, the shaft member can become misaligned in the vertical direction. As a result thereof, the shaft member is subject to oscillations (i.e., periodic deviations) in the horizontal direction. Such oscillation results in a problem wherein the blood pump in its entirety vibrates undesirably and excessively. In addition, hemolysis can be caused in response to the oscillation.

SUMMARY OF THE INVENTION

An object of the present invention is to provide a method of manufacturing a centrifugal pump in which when a centrifugal force applying member rotates, a shaft member rotating together with the centrifugal force applying member can be reliably prevented from oscillating, and hemolysis can be reliably prevented or restrained from being caused between the shaft member and each of a first bearing and a second bearing.

Such an object is realized through a method of manufacturing a centrifugal pump including a housing that is configured to define a hollow body cavity to provide a pumping chamber. A blood inlet port communicates with the hollow body cavity where blood flows in, and a blood outlet port communicates with the hollow body cavity where blood flows out. A centrifugal force applying member (i.e., impeller) is rotatably accommodated in the hollow body cavity and rotates so as to apply centrifugal force to the blood. A support mechanism supports the centrifugal force applying member to provide rotation with respect to the housing. The support mechanism comprises a shaft member installed at a rotational center axis of the centrifugal force applying member, a first bearing which rotatably supports one end portion of the shaft member, and a second bearing which rotatably supports the other end portion of the shaft member.

The housing is comprised of a lid member into which the first bearing is installed and a bottom member into which the second bearing is installed. For joining the housing, the lid member and bottom member are initially placed into an assembly state in which the rotary shaft member is fitted between the first and second bearings. While in the assembly state, the lid member and bottom member are compressed in a direction in which the lid member and the bottom member approach each other, and then the lid member and the bottom member are joined to each other in the compressed state.

In the above method of manufacturing a centrifugal pump, a separation distance between the first bearing and the second bearing while in the assembly state after the assembling step is a separation distance $D_0$, corresponding to an overall distance between the opposite ends of the rotary shaft member which are in contact with the bearings. After being affixed in the compressed state, the rotary shaft member maintains the separation distance $D_0$ between the first and second bearings, but if not for the presence of the rotary shaft member a separation distance $D_1$ would naturally result between the first bearing and the second bearing which is smaller than the separation distance $D_0$.

In the method of manufacturing a centrifugal pump, the compressed state provides a compression corresponding to separation distance $D_1$ being equal to or less than 99% of the separation distance $D_0$.

In the method of manufacturing a centrifugal pump, easily-deformable portions are provided in the lid member and the bottom member that can be individually deformed due to the compression at a boundary portion between the lid member and the bottom member. In the joining step, the separation distance $D_1$ is adjusted by causing the easily-deformable portion to be deformed.

In the method of manufacturing a centrifugal pump, in the joining step, the lid member and the bottom member are welded in the assembly state by irradiating a spot in the vicinity of the boundary portion between the lid member and the bottom member with laser light (e.g., using a semiconductor laser).

In the method of manufacturing a centrifugal pump, each of the lid member and the bottom member has light-transmitting characteristics. In the joining step, welding is performed in a state where an optical absorption material is interposed in the boundary portion, by irradiating the optical absorption material with the laser light.

Advantageous Effect of Invention

According to the present invention, compression is performed in the direction in which the lid member and the bottom member approach each other in the assembly state, and the lid member and the bottom member are joined. In other words, the lid member and the bottom member are joined in a state where the shaft member is tightened. Accordingly, while the centrifugal pump is in use, whenever the internal pressure in the housing rises and the housing expands in the rotary shaft axial direction, the shaft member can be prevented or restrained from oscillating due to the expansion of the housing, because the interface between the bearings and the shaft member is tightened in advance and there is no increase in the actual separation distance between the bearings (i.e., the expansion merely reduces the compression load on the shaft member). Therefore, hemolysis can be reliably prevented or restrained from being caused between the shaft member and each of the first bearing and the second bearing.

DETAILED DESCRIPTION OF PREFERRED EMBODIMENTS

Hereinafter, a method of manufacturing a centrifugal pump according to the present invention will be described in detail based on a suitable embodiment illustrated in the accompanying drawings.

First Embodiment

Figure 1:
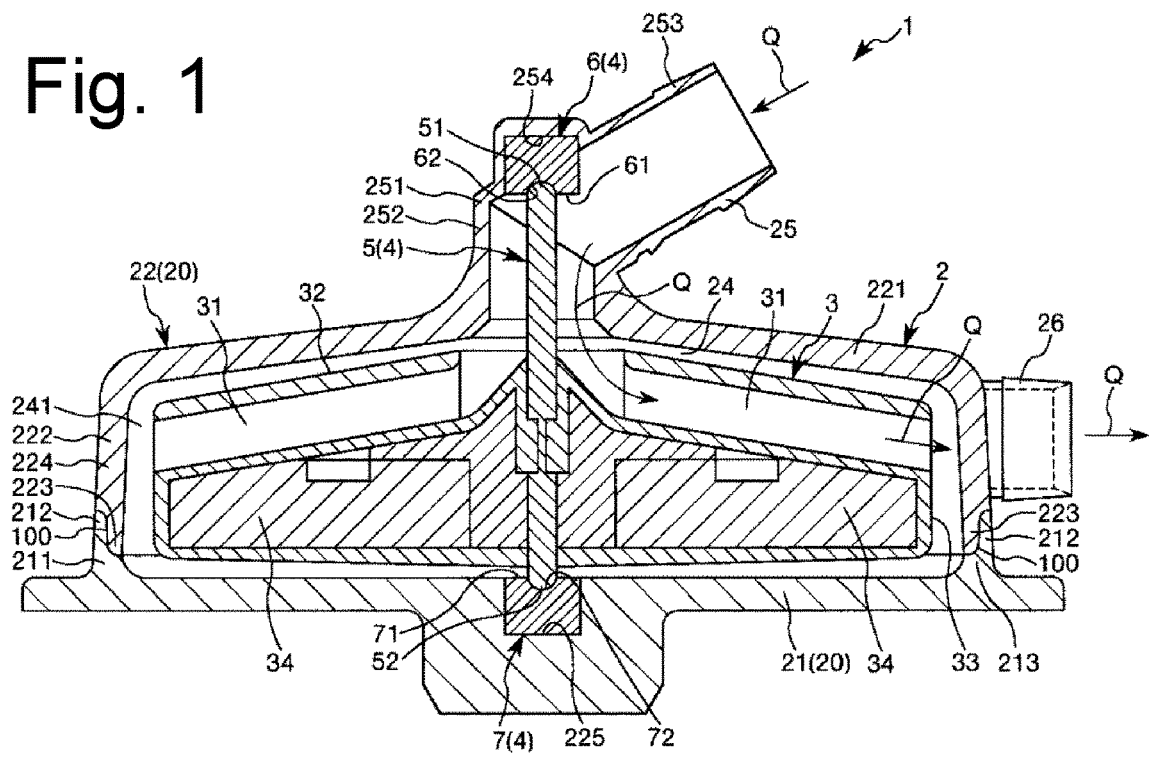
FIG. 1 is a cross-sectional side view illustrating an embodiment of a centrifugal pump manufactured through a manufacturing method according to the present invention.
Figure 2:
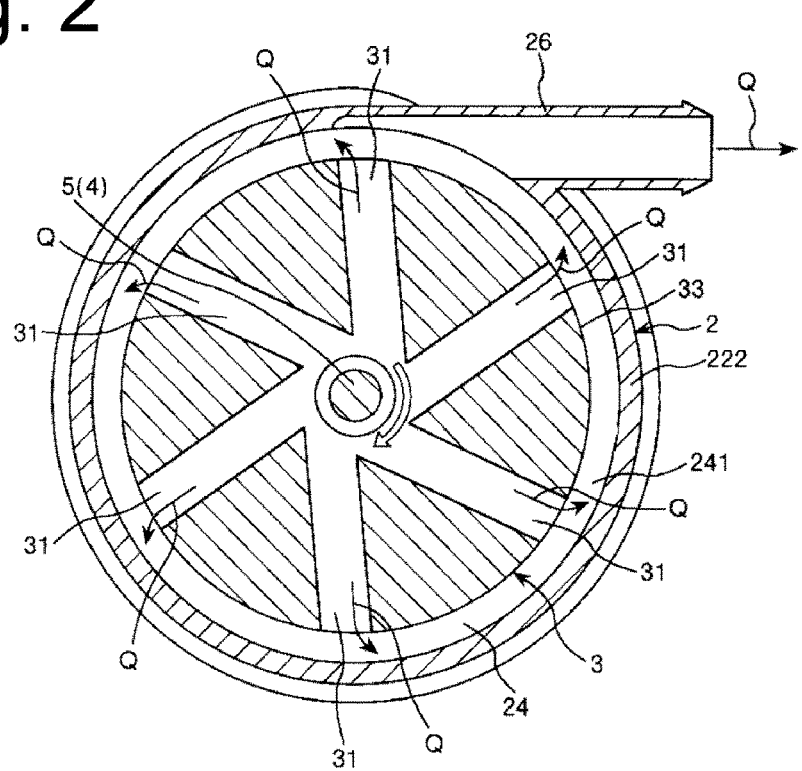
FIG. 2 is a cross-sectional plan view of the centrifugal pump illustrated in FIG. 1.
Figure 3:
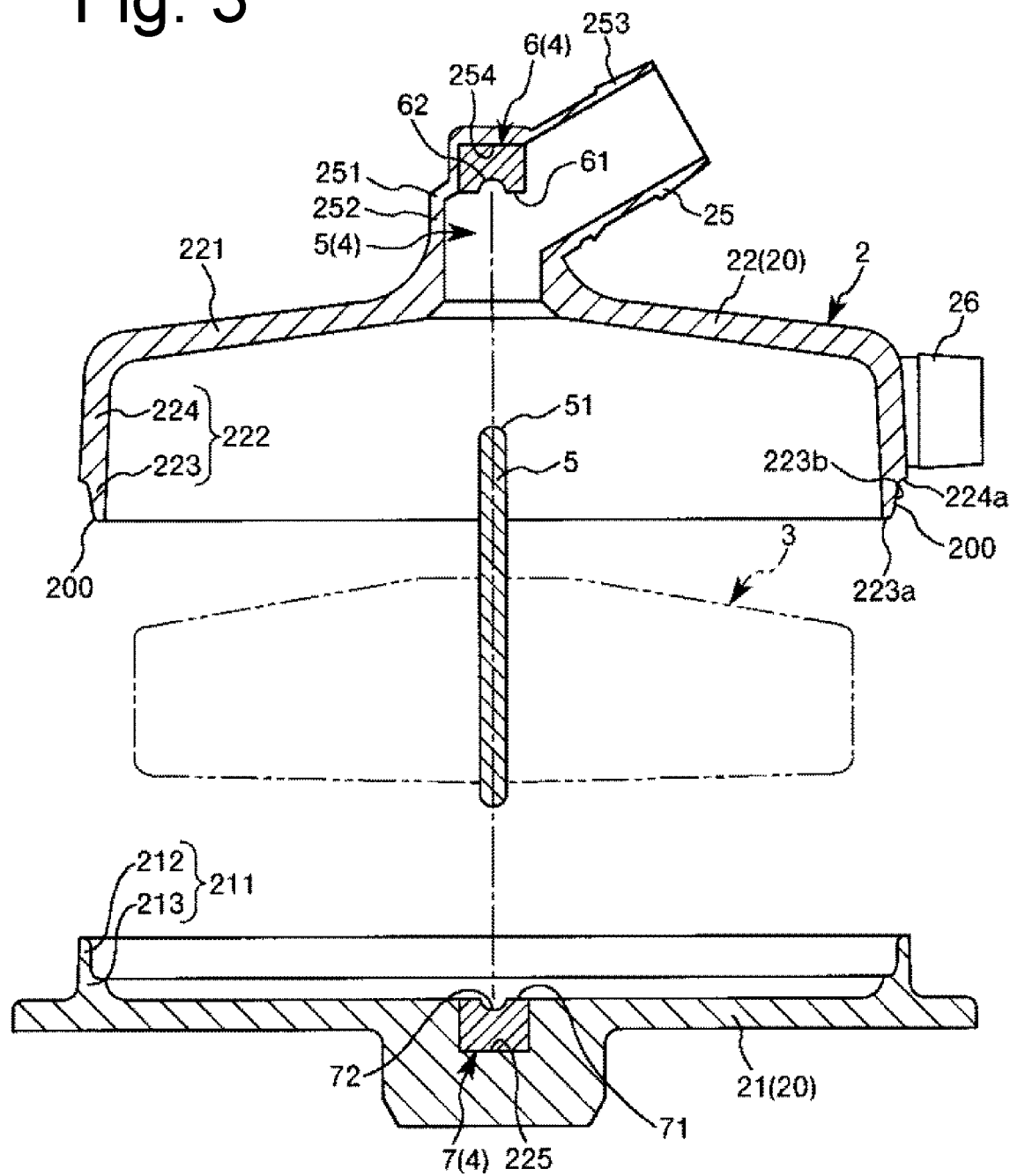
FIG. 3 is a longitudinal sectional view illustrating a method of manufacturing a centrifugal pump according to the present invention, wherein the view illustrates a preparing step.
Figure 4:
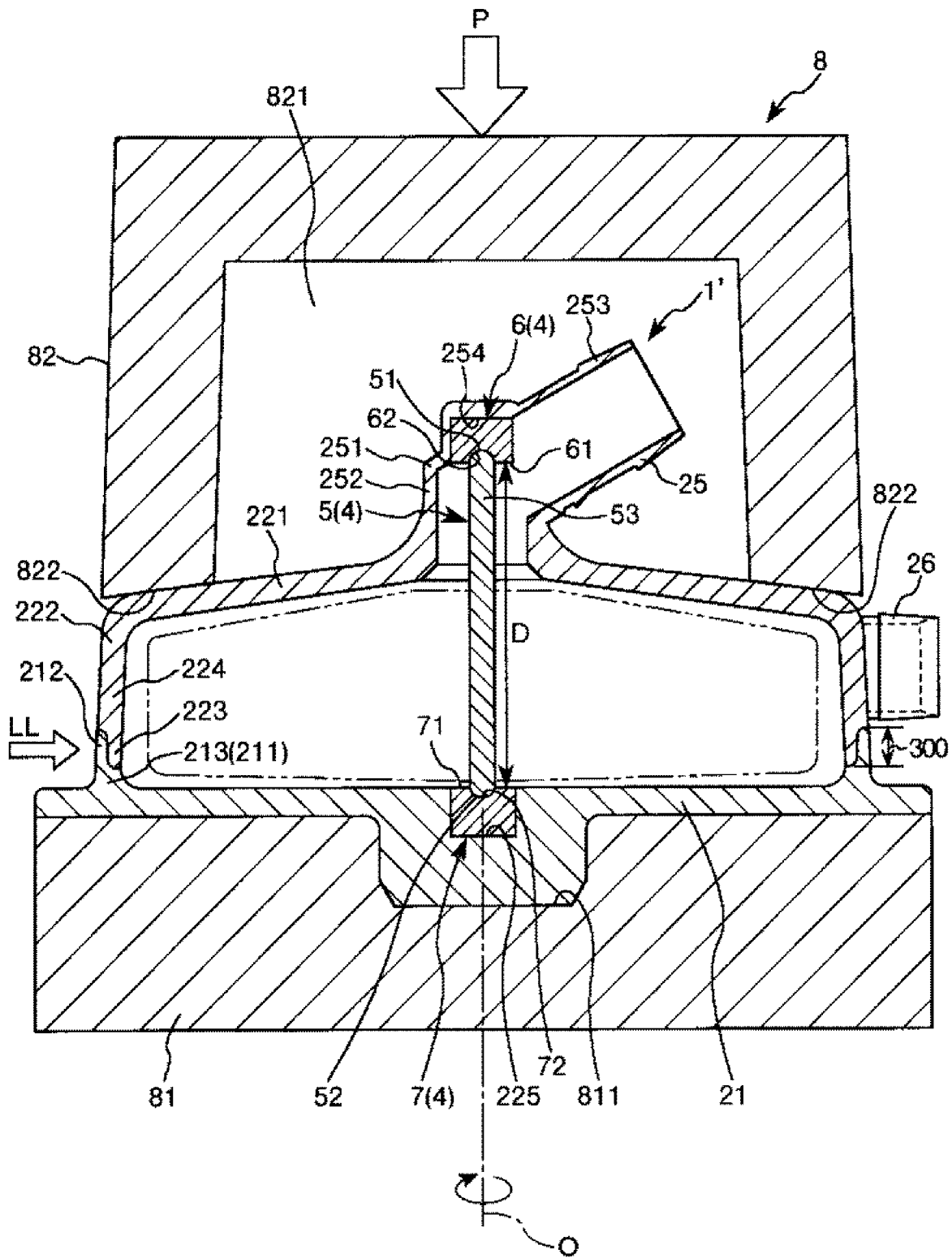
FIG. 4 is a longitudinal sectional view illustrating the method of manufacturing a centrifugal pump according to the present invention, wherein the view illustrates compression and joining steps.
Figure 5A:
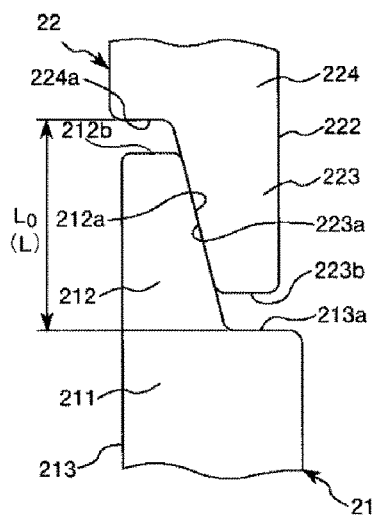
FIGS. 5A, 5B, and 5C are longitudinal sectional views illustrating the method of manufacturing a centrifugal pump according to the present invention, and are partially enlarged views of a housing illustrated in FIG. 3.
Figure 5B:
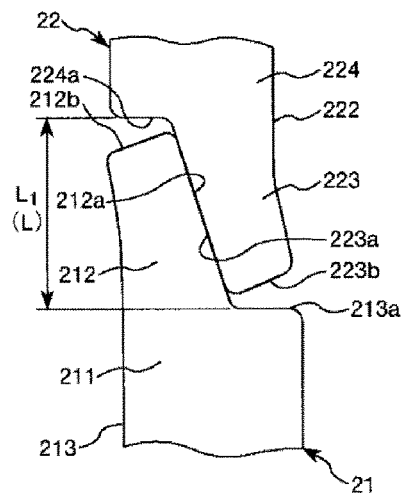
Figure 5C:
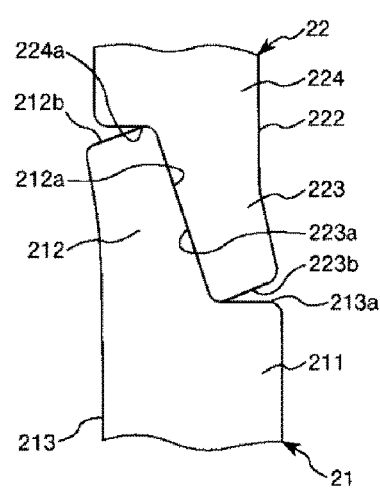

FIG. 1 is a cross-sectional side view illustrating an embodiment of a centrifugal pump manufactured through a manufacturing method according to the present invention. FIG. 2 is a cross-sectional plan view of the centrifugal pump illustrated in FIG. 1. FIG. 3 is a longitudinal sectional view illustrating a method of manufacturing a centrifugal pump according to the present invention, and the view illustrates a preparing step. FIG. 4 is a longitudinal sectional view illustrating the method of manufacturing a centrifugal pump according to the present invention, and the view illustrates a joining step. FIG. 5 is a longitudinal sectional view illustrating the method of manufacturing a centrifugal pump according to the present invention, and is a partially enlarged view of a housing illustrated in FIG. 3.

Note that, hereinafter, for convenience of description, in FIGS. 1, and 3 to 5, the upper side will be referred to as "top" or "upward" and the lower side will be referred to as "bottom" or "downward".

A centrifugal pump 1 illustrated in FIG. 1 includes a housing 2 which is configured with a hollow body, a rotary body (impeller) 3 which is rotatably accommodated in the housing 2, and a support mechanism 4 which supports the rotary body 3 such that the rotary body 3 can rotate with respect to the housing 2. Hereinafter, a configuration of each portion will be described.

The housing 2 is provided with a housing main body 20, a blood inlet port 25 through which blood Q flows in, and a blood outlet port 26 through which the blood Q flows out.

The housing main body 20 is formed of a flat cylindrical member and is provided with a bottom member 21, and a lid member 22 in which the blood inlet port 25 and the blood outlet port 26 are formed such that these are joined in an assembly.

The bottom member 21 has a disk shape and is provided with a side wall (first wall portion) 211 which is formed so as to protrude from an edge portion on an upper surface thereof and extends in the circumferential direction. In addition, the side wall 211 is provided with a thin distal portion 212 having a reduced thickness at an upper end thereof, and a thicker base portion 213 having a constant thickness. The thin portion 212 is provided throughout the entire circumference of the housing main body 20 in the circumferential direction. In addition, the thin distal portion 212 gradually reduces in thickness toward the upper side, and an inner peripheral surface 212a thereof inclines (refer to FIG. 5).

The lid member 22 is provided with a top plate 221 and a side wall (second wall portion) 222 which is formed so as to protrude from an edge portion on a lower surface of the top plate 221 and extends in the circumferential direction. In addition, the side wall 222 is provided with a thin distal portion 223 which is provided at a lower end portion of a thicker base portion 224 having a constant thickness. The thin distal portion 223 is provided throughout the entire circumference of the housing main body 20 in the circumferential direction. In addition, the thin distal portion 223 gradually reduces in thickness toward the lower side, and an outer peripheral surface 223a thereof inclines (refer to FIG. 5).

In addition, in the assembly state, the thin distal portion 212 is positioned outside of and adjacent the thin distal portion 223. A boundary portion interposed between the thin portion 212 and the thin portion 223 is formed so as to be a welded portion 100 which is preferably welded by irradiating a spot in the vicinity of the boundary portion with laser light. The welded portion 100 is formed throughout the entire circumference of the housing main body 20. The detailed description thereof will be given later.

A flat, open space (hollow body cavity) surrounded by the bottom member 21 and the lid member 22 serves as a pump chamber 24.

In addition, the blood inlet port 25 and the blood outlet port 26 individually communicate with the pump chamber 24. The blood Q which has flowed in through the blood inlet port 25 can flow out through the blood outlet port 26 via the pump chamber 24.

As illustrated in FIG. 1, the blood inlet port 25 is tubularly (cylindrically) formed so as to protrude from a central portion of the top plate 221 (one end portion). An intermediate portion of the blood inlet port 25 in the longitudinal direction is bent. A bent portion 251 serves as a boundary portion and divides the blood inlet port 25 into a proximal portion 252 on the top plate 221 side and a connection portion 253 on a side opposite thereto. The connection portion 253 is provided so as to incline with respect to a rotary axis of the rotary body 3. For example, a tube configuring a blood circuit can be connected to the connection portion 253.

As illustrated in FIG. 2, the blood outlet port 26 is tubularly formed so as to protrude from the outer peripheral surface (outer peripheral portion) of the side wall 222. The blood outlet port 26 protrudes toward a tangential direction of the outer peripheral surface of the side wall 222.

In the pump chamber 24 of the housing main body 20, the rotary body 3 having a disk shape is concentrically disposed. The rotary body 3 is a centrifugal force applying member which rotates so as to apply centrifugal force to the blood Q.

As illustrated in FIG. 2, the rotary body 3 is provided with a plurality of blood flow paths 31 (six in the illustrated configuration) through which the blood Q passes. The blood flow paths 31 are formed radially from the center of the rotary body 3. In addition, portions of the blood flow paths 31 on the center side of the rotary body 3 meet (intersect) each other and are open on an upper surface 32 of the rotary body 3. Meanwhile, portions of the blood flow paths 31 on a side opposite to the center side of the rotary body 3 are open on an outer peripheral surface 33 of the rotary body 3. In addition, a gap 241 is formed between the outer peripheral surface 33 of the rotary body 3 and an inner peripheral surface of the side wall 222 of the housing 2.

When the above-described rotary body 3 rotates clockwise around a shaft member 5 as illustrated in FIG. 2 in which the housing 2 is viewed from above, the blood Q flowing in through the blood inlet port 25 enters each of the blood flow paths 31 from the portion on the center side of the rotary body 3, and the blood Q flows down through the blood flow paths 31 upon reception of centrifugal force. The flowed-down blood Q flows out to the inside of the gap 241. Thereafter, the blood Q receives clockwise rotary force in the gap 241 as illustrated in FIG. 2. When the blood Q arrives at the blood outlet port 26, the blood Q is reliably discharged through the blood outlet port 26.

As illustrated in FIG. 1, in the rotary body 3, magnets are respectively installed at portions of the blood flow paths 31 on the lower side. Note that, in the configuration illustrated in FIG. 1, a plurality of (for example, six) permanent magnets 34 are adopted. When the centrifugal pump 1 is driven, the bottom member 21 of the housing 2 is caused to be the lower side such that the below-described shaft member 5 becomes parallel to the vertical direction, and the centrifugal pump 1 is mounted with external drive means (not illustrated). In this mounted state, the centrifugal pump 1 is used. For example, the external drive means is provided with a motor and a permanent magnet which is interlocked with the motor. The permanent magnet and the permanent magnets 34 built in the centrifugal pump 1 attract each other due to magnetic force. When the motor rotates in such a state, rotary force thereof is transferred via the magnets attracting each other, and thus, the rotary body 3 can also rotate.

Note that, the diameter of the rotary body 3 is not particularly limited. For example, the diameter preferably ranges from 20 to 200 mm and more preferably ranges from 30 to 100 mm. The thickness of the rotary body 3 is not particularly limited. For example, the thickness preferably ranges from 3 to 40 mm and more preferably ranges from 5 to 30 mm. The maximum speed of the rotary body 3 is not particularly limited. For example, the maximum speed preferably ranges from 2,000 to 6,000 rpm and more preferably ranges from 2,500 to 5,000 rpm.

In addition, the configuration material of the rotary body 3 and the housing 2 is not particularly limited. For example, examples of the configuration material include an acryl-based resin such as rigid polyvinyl chloride, polyethylene, polypropylene, polystyrene, polycarbonate, an acrylic resin, and polymethyl methacrylate (PMMA); polyester such as polyethylene terephthalate (PET) and polybutylene terephthalate (PBT); polysulfone; and various types of rigid resins such as polyarylate. In addition, among the above-referenced configuration materials, polycarbonate and an acrylic resin are particularly preferable in compatibility with the blood Q, and excellent transparency and molding processability. Note that, the constituent material of the housing 2 from among the above-referenced resin materials is a material having light-transmitting characteristics and having a flexibility which exhibits the above-mentioned expansion in the presence of pressurized blood with housing 2.

Particularly, the fusing point during welding of the constituent material of the housing 2 (the bottom member 21 and the lid member 22) is not particularly limited. The fusing point thereof preferably ranges from approximately 200° C. to 400° C. and more preferably ranges from approximately 250° C. to 350° C. When such a material is adopted, fixing after welding can be promptly performed, and thus, welding properties of the welded portion 100 and the uniformity of welding are further improved.

As illustrated in FIG. 1, the rotary body 3 is supported via the support mechanism 4 so as to be rotatable with respect to the housing 2. The support mechanism 4 is provided with the shaft member 5, a first bearing 6 which rotatably supports the upper end portion (one end portion) of the shaft member 5, and a second bearing 7 which rotatably supports the lower end portion (the other end portion) of the shaft member 5.

The shaft member 5 is installed at the rotation center of the rotary body 3. The shaft member 5 is configured to include a rod-like member having both end portions rounded. In a case where a ceramic is adopted as the constituent material of the shaft member 5, whenever both the end portions of the shaft member 5 are subjected to grinding, then the sliding characteristics of both the end portions during rotation of the shaft member 5 are improved. In addition, in a case where a metallic material is adopted as the configuration material of the shaft member 5, after being subjected to grinding, both the end portions of the shaft member 5 may be coated with diamond-like carbon (DLC) or titanium, for example. Accordingly, sliding characteristics and durability of both the end portions during rotation of the shaft member 5 are improved.

The first bearing 6 is fixedly installed in a first bearing installation portion (receptacle) 254 which is formed so as to be recessed in an inner peripheral portion of the connection portion 253 of the blood inlet port 25. The first bearing 6 has a block shape, and has a curved recess surface 62 on a lower surface 61 which is depressed along the curved shape of an upper end surface 51 of the shaft member 5.

The second bearing 7 is fixedly installed in a second bearing installation portion (receptacle) 225 which is formed so as to be recessed in a central portion of the bottom member 21 of the housing 2. The second bearing 7 has a block shape, and has a curved recess surface 72 on an upper surface 71 which is depressed along the curved shape of a lower end surface 52 of the shaft member 5.

Note that, the method of fixing the first bearing 6 and the second bearing 7 in receptacles 254 and 225 is not particularly limited. Examples of the fixing method include a method performed through press fitting, a method performed through adhering (adhering performed with an adhesive or a solvent), a method performed through welding (heat-welding, high-frequency welding, ultrasound welding, and the like), and a method performed through insert molding.

Subsequently, the method of manufacturing the centrifugal pump 1 will be described. In particular, a preferred method of manufacturing the centrifugal pump 1 includes

[1]a preparing step, [2]an optical absorption material supplying step, [3]an assembling step, and [4]a joining (e.g., welding) step.

In the Preparing Step as partially illustrated in FIGS. 3 and 4, the bottom member 21, the lid member 22, the rotary body 3, and the support mechanism 4 (which have been prefabricated) are arranged according to their intended operational positions. These components are brought together along the central rotational axis as shown in FIG. 3 into a preliminary assembly state and then installed into a jig 8 as shown in FIG. 4.

The jig 8 is provided with a holding tool 81 which holds the bottom member 21, and a compression tool 82 which is part of a machine press (not shown) for generating a pressing force P to compress the bottom member 21 and the lid member 22.

The holding tool 81 has a disk shape (block shape), and a recessed portion 811 on the upper surface thereof receives the lower end portion of the bottom member 21. In addition, the holding tool 81 is fixed to a turntable (not illustrated) so as to be rotatable around the rotation center of the rotary body 3.

The cross-sectional shape of the compression tool 82 forms a circular bottomed tube shape provided with an inner space 821 such that the blood inlet port 25 can be accommodated therein. The inner space 821 functions as a venting portion for the blood inlet port 25 when the housing main body 20 is pressurized. In addition, a lower end surface 822 of the compression tool 82 inclines along the shape of the top plate 221 of the lid member 22.

In an Optical Absorption Material Supplying Step performed while the components of the pump are arranged as shown in FIG. 3, the interface surface of the thin distal portion 223 of the lid member 22 is coated (covered) with an optical absorption material 200 which absorbs laser light. Examples of the optical absorption material 200 include powder such as carbon black, a liquefied (pasty) material including the aforementioned powder or the below-described dye, or a sheet-like (layered) material including the aforementioned powder or the aforementioned dye.

In the present embodiment, a liquefied (pasty) optical absorption material 200 is preferably adopted, and an end surface 223b of the thin portion 223, the outer peripheral surface 223a of the thin portion 223, and an end surface 224a of the constant thickness portion 224 are coated with the optical absorption material 200. The end surface 223b, the outer peripheral surface 223a, and the end surface 224a are continuously formed and the boundaries therebetween are preferably rounded. Accordingly, when coating is performed with the optical absorption material 200, air bubbles can be prevented or restrained from being entrained with the optical absorption material.

In addition, when the liquefied (pasty) optical absorption material 200 is adopted, the shape of the optical absorption material 200 freely conforms to the surface to be covered, thereby being suitable for a case where a surface to be coated is curved or bent in a different shape as in the present embodiment.

The coating method performed with the liquefied (pasty) optical absorption material 200 is not particularly limited. Any type of coating method such as spray coating (spray painting), brush coating, dipping, and dripping can be adopted.

Note that, for example, in a case where a sheet-like optical absorption material 200 is adopted, a sheet-like optical absorption material 200 which is punched (cut out) so as to have the same shape (annular) as the shape of the thin portion 223 is prepared, and the prepared sheet-like optical absorption material 200 is interposed between the thin portion 212 and the thin portion 223 in the assembling step described below. When the sheet-like optical absorption material 200 is adopted, an annular optical absorption material is prepared (manufactured) in advance, and the prepared optical absorption material may be mounted in a target site. Thus, there is an advantage in that the interposing operation is simpler than the case where a pasty optical absorption material 200 is adopted.

In addition, as an optical absorption material (laser optical absorption material) configuring the optical absorption material 200, materials (listed below) which do not impede the transparency of the welded portion 100 as much as possible can be adopted. As such an optical absorption material, a material which is less likely to absorb the visible light region (range from 0.4 μm to less than 0.7 μm) and indicates a high molar absorption coefficient in a narrow absorption band within a laser light wavelength region from 0.7 to 2.5 μm is preferably adopted. Examples of the optical absorption material include a dye such as a cyanine dye, a squarylium dye, and a croconium dye.

As specific examples, for example, the compound shown in Chemical Formula 1 described below can be adopted as the cyanine dye, the compound shown in Chemical Formula 2 described below can be adopted as the squarylium dye, and the compound shown in Chemical Formula 3 described below can be adopted as the croconium dye.

[Chem 1]

Chemical Formula 1

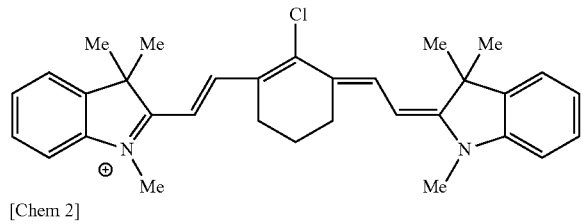

[Chem 2]

Chemical Formula 2

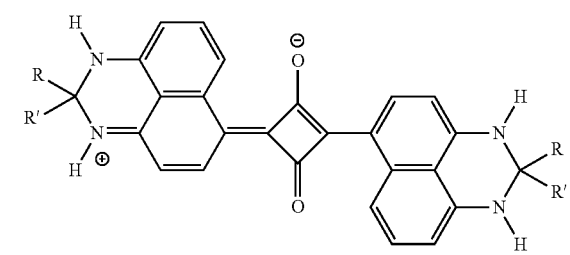

[Chem 3]

Chemical Formula 3

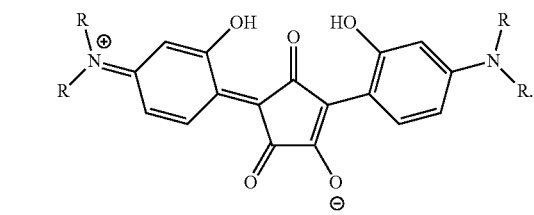

When the above-referenced laser optical absorption material is adopted as the optical absorption material 200, the transparency of the welded portion 100 can be maintained as much as possible since it is desirable to maintain visibility of the pumping chamber and its contents during use as a blood pump. Moreover, the welded portion 100 can be prevented from being colored, becoming conspicuous with respect to the bottom member 21 and the lid member 22 which are formed of a transparent material, and spoiling the sense of unity of the appearance.

In addition, when a separately prepared optical absorption material 200 is adopted, there is no need to directly color the bottom member 21 or the lid member 22 in order to cause laser light to be absorbed, and the bottom member 21 or the lid member 22 can be substantially transparent. Thus, visibility inside thereof can be sufficiently ensured.

In addition, as the optical absorption material 200, the same type of material as the housing 2, for example, a material obtained by kneading polycarbonate may be used so as to be supplied to the thin portion 223 through a molding method such as two-color molding.

In the Assembling Step as illustrated in FIG. 4, the bottom member 21 and the lid member 22 are assembled such that the rotary body 3 and the support mechanism 4 are internally accommodated. In this case, since the outer peripheral surface 223a of the lid member 22 is guided by the inner peripheral surface 212a of the bottom member 21, the outer peripheral surface 223a can be easily positioned with respect to the bottom member 21. Accordingly, the assembly state can be easily realized.

The centrifugal pump 1 in the assembly state (hereinafter, the centrifugal pump 1 in the assembly state will also be referred to as "centrifugal pump 1'") is fixed to the inside of the recessed portion 811 of the holding tool 81, and the lower end surface 822 of the compression tool 82 is disposed on the upper surface of the top plate 221.

In a Joining Step with centrifugal pump 1' in the assembly state as illustrated in FIG. 4 and with a pressing force P acting upon compression tool 82 as described in more detail below, the optical absorption material 200 is irradiated with laser light LL. The optical absorption material 200 is irradiated with the laser light LL which has been transmitted through the thin portion 212 of the bottom member 21. In the irradiated optical absorption material 200, the laser light LL is efficiently absorbed into the optical absorption material 200 and is converted into heat. Therefore, welding can be efficiently performed with a low power output.

In addition, a light source of the laser light LL is fixed, and the holding tool 81 is rotated together with the centrifugal pump 1', thereby performing irradiation with the laser light LL throughout the entire circumference of the optical absorption material 200. Accordingly, the bottom member 21 and the lid member 22 can be welded throughout the entire circumference, that is, the welded portion 100 can be formed throughout the entire circumference of the housing 2. Therefore, improvement of welding strength (joining strength) can be achieved.

In addition, as illustrated in FIG. 4, irradiation with the laser light LL is performed throughout the overall length of an overlapping portion 300 in the vertical direction in FIG. 4, in which the thin portion 212 of the bottom member 21 and the thin portion 223 of the lid member 22 overlap each other in the radial direction of the housing 2. Accordingly, the welded portion 100 can be formed through a simple method in which irradiation is performed with the laser light LL and the centrifugal pump 1' is rotated once.

In addition, a joining area (welding area) can be maximized as much as possible by joining the thin portion 212 and the thin portion 223. Therefore, the bottom member 21 and the lid member 22 can be joined with further enhanced joining strength. Moreover, since the thin portion 212 is thin in thickness, when the laser light LL is transmitted therethrough, attenuation can be limited.

Particularly, as illustrated in FIG. 4, the inner peripheral surface 212a of the thin portion 212 and the outer peripheral surface 223a of the thin portion 223 are provided so as to individually incline with respect to the rotation center of the rotary body 3. Accordingly, in a case where the internal pressure of the housing 2 rises while the centrifugal pump 1 is in use, force acts in a direction in which the outer peripheral surface 223a of the thin portion 223 is pressed against the inner peripheral surface 212a of the thin portion 212. Therefore, it is possible to reliably prevent force from being added in a direction in which the bottom member 21 and the lid member 22 are separated from each other and to reliably prevent an occurrence of a crack caused due to the force thereof and damage to the welded portion 100.

The type of laser light LL for irradiation is not particularly limited. Examples of the laser light LL for irradiation include a semiconductor laser, a $CO_2$ laser, a YAG laser, and an excimer laser. Particularly, among the above-referenced lasers, a semiconductor laser has favorable energy efficiency due to its long service life.

The wavelength of the laser light LL for irradiation substantially depends on the type of laser light LL. In a case of a semiconductor laser, the wavelength thereof preferably ranges from approximately 800 to 1,000 nm.

The beam diameter of the laser light LL is not particularly limited. The beam diameter thereof is preferably the same as or slightly greater than the length of the overlapping portion 300 in the vertical direction in FIG. 4. Accordingly, through the simple method in which the overlapping portion 300 is irradiated with the laser light LL, and the bottom member 21 and the lid member 22 are rotated, irradiation with the laser light LL can be reliably performed throughout the overall length of the optical absorption material 200 in the vertical direction in FIG. 4. Therefore, welding can be easily performed. Thus, a centrifugal pump 1 can be obtained through the above-described steps.

Incidentally, when a centrifugal pump of a conventional design is in use, the internal pressure in the housing 2 rises and the housing 2 tends to expand in a rotary axis O direction. Therefore, a separation distance D between the lower surface 61 of the first bearing 6 and the upper surface 71 of the second bearing 7 is lengthened by an incremental expansion distance proportional to the internal pressure, and the shaft member 5 is misaligned in the vertical direction. Moreover, the shaft member 5 oscillates in the horizontal direction as well. As a result thereof, hemolysis may be caused between the upper end surface 51 of the shaft member 5 and the curved recess surface 62 of the first bearing 6, and between the lower end surface 52 of the shaft member 5 and the curved recess surface 72 of the second bearing 7 respectively. In the present invention, such a problem can be prevented in advance. Hereinafter, description thereof will be given.

As illustrated in FIG. 4, in the present invention, in the joining step, the compression tool 82 is used so as to perform compression with a pressurizing force P in the direction in which the bottom member 21 and the lid member 22 approach each other, and welding is performed as described above while in the compressed state. Under compression, separation distance D between the lower surface 61 of the first bearing 6 and the upper surface 71 of the second bearing 7 is substantially unchanged due to the resistance of shaft member 5. However, the outer radial portions of housing 2 are slightly deformed under compression so that walls 222 and 211 engage beyond the initial position obtained in the assembly state. After welding, a compression "preloading" is present between shaft member 5 and bearings 6 and 7.

As illustrated in FIG. 5(*a*), in the assembly state before compression is performed, the lid member 22 is in a state of being disposed on the bottom member 21. In such a state, the positional relationship between the bottom member 21 and the lid member 22 is temporarily restricted by the arrangement of the inner peripheral surface 212*a* of the thin portion 212 and the outer peripheral surface 223*a* of the thin portion 223. In addition, in this case, a distance L between the end surface 224*a* of the constant thickness portion 224 and an end surface 212*b* of the constant thickness portion 213 is indicated as an initial, uncompressed distance $L_0$.

As illustrated in FIG. 5(*b*), when compression is performed, the lid member 22 is pressed toward the bottom member 21, that is, the lid member 22 is tightened. In accordance with the tightening, the inner peripheral surface 212*a* of the thin portion 212 and the outer peripheral surface 223*a* of the thin portion 223 slide with respect to each other. In this case, as illustrated in FIG. 5(*b*), the thin portion 223 is warped and deformed inward, and the thin portion 212 is warped and deformed outward. As a result thereof, the distance L after the joining step is shown as a distance $L_1$ which is shorter than the distance $L_0$. In addition, when the distance L is reduced from the uncompressed distance $L_0$ to the compressed distance $L_1$, the separation distance D between the lower surface 61 of the first bearing 6 and the upper surface 71 of the second bearing 7 that would be obtained if not for the presence of shaft member 5 likewise reduces to an unhindered separation distance $D_1$ which is shorter than a separation distance $D_0$ in the assembly state. In other words, the change in wall interface distance L from distance $L_0$ to the compressed distance $L_1$ determined the hypothetical, unhindered change in the bearing separation distance D. Preferably, this change in distance is approximately equal to the incremental expansion distance that would otherwise occur between bearings 6 and 7 when pressurized during use of the blood pump if the preloading were not present.

In this manner, in the centrifugal pump 1, since the thin portion 212 and the thin portion 223 are easily-deformable portions which are deformed prior to the peripheral portions, the unhindered separation distance D can be adjusted by being compressed.

In addition, when the bottom member 21 and the lid member 22 are joined while in a position corresponding to the unhindered separation distance $D_1$, a joined state is obtained wherein a pilot pressure in the compression direction is continuously applied to the housing 2. In the centrifugal pump 1 obtained through the above-described method, when the internal pressure rises while being in use and the separation distance D would tend to increase due to expansion of the housing 2 in the rotary axis O direction, the shaft member 5 can be prevented or restrained from moving in the rotary axis O direction due to the increase of the separation distance D, because the preload force applied by the bottom member 21 and the lid member 22 against shaft member 5 and bearing 6 and 7 counteracts the tendency of expansion to increase the separation distance $D_0$. Therefore, hemolysis caused in accordance with movement of the shaft member 5 can be prevented or restrained. Moreover, welding strength can be further enhanced by performing compression and welding together.

In addition, the unhindered separation distance $D_1$ preferably ranges from 97% to 99% of the separation distance $D_0$ and more preferably ranges from 97.5% to 98.5%. In other words, a difference between the assembly distance $L_0$ and the compressed distance $L_1$ preferably ranges from 97% to 99% of the separation distance $D_0$ and more preferably ranges from 97.5% to 98.5%. Accordingly, hemolysis can be reliably prevented. When the unhindered separation distance $D_1$ (as controlled by the difference $L_0$-$L_1$) drops below the lower limit value, due to the configuration material of the first bearing 6, the second bearing 7, and the shaft member 5 in some cases, there is a possibility that the first bearing 6 and the second bearing 7 is damaged. Meanwhile, in a case where the separation distance $D_1$ (as controlled by the difference $L_0$-$L_1$) exceeds the upper limit value, there is a possibility that the effect of the present invention is not sufficiently obtained.

In addition, due to the configuration material of the housing 2 in some cases, it is possible to consider that the thin portion 212 and the thin portion 223 may break depending on the magnitude of the pressurizing force P. In the centrifugal pump 1, as illustrated in FIG. 5(*c*), when the end surface 224*a* of the constant thickness portion 224 and the end surface 212*b* of the thin portion 212 are attached to each other and an end surface 213*a* of the constant thickness portion 213 and the end surface 223*b* of the thin portion 223 are attached to each other, the tightening (compression) limit can be restricted. Accordingly, the thin portion 212 and the thin portion 223 can be reliably prevented from being excessively deformed and broken.

Moreover, proximal portions of the thin portion 212 and the thin portion 223 are thicker than the end portions. In other words, rigidity of the thin portion 212 and the thin portion 223 is higher in the proximal portions. Accordingly, breakage can be more reliably prevented.

In addition, in the present embodiment, when welding is performed, the compression tool 82 compresses the bottom member 21 and the lid member 22 with the compression force P in the direction of approaching each other. Accordingly, welding strength can be further enhanced. In addition, in this case, the compression tool 82 presses the edge portion of the top plate 221 of the lid member 22 with the lower end surface 822, that is, a spot in the vicinity of a root portion of the side wall 222. Accordingly, the compression force (restraining force) of the compression tool 82 is efficiently transferred to the side wall 222. Therefore, positional misalignment of the bottom member 21 and the lid member 22 in the circumferential direction caused due to pressing can be prevented, and the boundary portion between the bottom member 21 and the lid member 22 can be uniformly pressed as much as possible throughout the entire circumference of the housing 2.

In this manner, according to the present invention, compression is performed in the direction in which the bottom member 21 and the lid member 22 in the assembly state approach each other, and the bottom member 21 and the lid member 22 are joined. In other words, the bottom member 21 and the lid member 22 are joined in a state where the shaft member 5 is tightened and pilot pressure is applied. Accordingly, while the centrifugal pump 1 is in use, even if the internal pressure in the housing 2 rises and the housing 2 expands in the rotary axis direction, the increased internal pressure can be cancelled as much a portion as the shaft member 5 is tightened in advance. Therefore, the shaft member 5 can be prevented or restrained from oscillating due to the expansion of the housing 2. Therefore, hemolysis can be reliably prevented or restrained from being caused between the shaft member 5 and the first bearing 6, and between the shaft member 5 and the second bearing 7.

Note that, since the centrifugal pump 1 obtained through the above-described step is compression and joined, the centrifugal pump 1 retains residual stress, for example, ranging from approximately 1 to 200 MPa at room temperature (approximately 25° C.). For example, the residual stress can be detected through a known method such as X-ray diffractometry.

Particularly, in the centrifugal pump 1, since the residual stress is retained as described above, there is a tendency to cause defect such as a crack in the boundary portion between the bottom member 21 and the lid member 22, that is, the joint portion. As mentioned above, in the present embodiment, welding is performed through irradiation with the laser light LL. Accordingly, welding strength (joining strength) can be enhanced, and defect such as a crack can be prevented or restrained from occurring. In addition, there is little unevenness of joining (unevenness of welding), and welding defect such as a pinhole, partial peeling, and intermixed air bubbles is unlikely to occur. In addition, as in ultrasound welding, since no residue is generated during welding, when the centrifugal pump 1 is manufactured, there is no need to perform a step of washing (including washing, and drying and the like after washing) the centrifugal pump 1 in order to remove residue, and thus, the centrifugal pump 1 can be manufactured through simple and fewer steps. Moreover, joining can be favorably performed within a relatively short period of time compared to adhering performed with an adhesive and welding performed with a solvent.

Hereinbefore, the method of manufacturing a centrifugal pump according to the present invention has been described with reference to the illustrated embodiment. The present invention is not limited thereto. Each of the portions configuring the centrifugal pump can be replaced with an arbitrarily configured portion which can exhibit a similar function. In addition, an arbitrarily configured element (step) may be added thereto.

Note that, in the embodiment, the lid member and the bottom member are welded by performing irradiation with laser light. However, the present invention is not limited thereto. For example, the method of joining the lid member and the bottom member may be welding such as heat-welding, high-frequency welding, and welding performed with a solvent; adhering performed with an adhesive; or the like.

In addition, in the embodiment, the assembling step is performed after the optical absorption material supplying step is performed. However, the present invention is not limited thereto. The optical absorption material supplying step may be performed after the assembling step is performed. In this case, the optical absorption material can be interposed by utilizing a capillary phenomenon in the boundary portion between the bottom member and the lid member.

In addition, in the embodiment, in the optical absorption step, the optical absorption material is supplied to the thin portion of the lid member. However, the present invention is not limited thereto. The optical absorption material may be supplied to the thin portion of the bottom member, or the optical absorption materials may be supplied to both the thin portion of the bottom member and the thin portion of the lid member.

In addition, in the embodiment, the thin portion of the bottom member is positioned outside the thin portion of the lid member. However, the present invention is not limited thereto. The thin portion of the bottom member may be positioned on an inner side of the thin portion of the lid member.

EXAMPLES

Hereinafter, description will be given regarding specific examples of centrifugal pumps manufactured according to the present invention. Note that, the present invention is not limited thereto.

1. Preparation of Centrifugal Pump

Example 1

The centrifugal pump illustrated in FIGS. 1 to 5 was prepared. In this centrifugal pump, the housing (the bottom member and the lid member) and the centrifugal force applying member were formed of polycarbonate. The spring constant of the bottom member was 161 N/mm, and the spring constant of the lid member was 308 N/mm.

The first bearing and the second bearing were formed of super-high-molecular polyethylene, and the spring constants thereof were 273 N/mm. In addition, the heights of the first bearing and the second bearing in the rotary axis direction were 3.0 mm, the depth of the recessed portion in which the shaft member was inserted was 1.5 mm, and the curvature was 2.0.

The shaft member was formed of alumina, the outer diameter was 3 mm, and the curvatures of both the end portions were 1.5.

In addition, in the joining step, compression was performed such that the ratio $D_1/D_0$ between the separation distance $D_0$ and the unhindered separation distance $D_1$ became the rate indicated in Table 1.

Example 2

In the joining step, except that compression was performed the according to ratio $D_1/D_0$ indicated in Table 1, a centrifugal pump of Example 2 was obtained in a manner similar to Example 1 described above.

Example 3

In the joining step, except that compression was performed according to the ratio $D_1/D_0$ indicated in Table 1, a centrifugal pump of Example 3 was obtained in a manner similar to Example 1 described above.

Example 4

In the joining step, except that compression was performed according to the ratio $D_1/D_0$ indicated in Table 1, a centrifugal pump of Example 4 was obtained in a manner similar to Example 1 described above.

Comparative Example 1

In the joining step, compression was performed according to the ratio $D_1/D_0$ indicated in Table 1, that is, excessive compression was performed, and a centrifugal pump of Comparative Example was obtained in a manner similar to Example 1 described above.

Comparative Example 2

In the joining step, compression was not performed, and a centrifugal pump of Comparative Example 2 was obtained in a manner similar to Example 1 described above.

2. Evaluation

In a simulated usage state, the centrifugal pumps of Examples 1 to 4 and Comparative Examples 1 and 2 were subjected to measurement in order to determine whether or not hemolysis is caused under the conditions in which the speed of the shaft member was 2600 rpm and the flow rate of blood was 8 L/min.

Moreover, the centrifugal pumps of Examples 1 to 4 and Comparative Examples 1 and 2 were subjected to general evaluation in accordance with the evaluation criteria 1 described below, in order to determine whether or not each of the centrifugal pumps is suitable for practical use.

Evaluation Criteria 1

A: much more excellent than the existing centrifugal pumps.
B: more excellent than the existing centrifugal pumps.
C: same as or poorer than the existing centrifugal pumps.

Table 1 shows an evaluation result 1 thereof.

TABLE 1

|  | Comparative Example 1 | Example 1 | Example 2 | Example 3 | Example 4 | Comparative Example 2 |
|---|---|---|---|---|---|---|
| Ratio $D_1/D_0$ | 96 | 97.5 | 97 | 98.5 | 99 | 100 |
| Evaluation | C | B | A | A | B | C |

As clearly seen in Table 1, the result shows that the centrifugal pumps of Examples 2 and 3 among Examples 1 to 4 are greatly suitable for practical use, and subsequent thereto, the centrifugal pumps of Examples 1 and 4 are suitable for practical use.

Note that, in the present invention, it has been checked that a centrifugal pump more excellent than the existing centrifugal pumps can be obtained as long as compression is performed in the joining step.

In addition, in the above description, the present invention has been described with reference to the suitable embodiment. The present invention is not limited to the embodiment. It is not necessary to mention that various modifications and changes can be made without departing from the scope and the gist of the present invention.

What is claimed is:

1. A method of manufacturing a centrifugal pump, wherein the centrifugal pump includes a housing to defining a hollow body cavity as a pumping chamber, a blood inlet port, a blood outlet port, a centrifugal force applying member rotatably accommodated in the pumping chamber, and a support mechanism that supports the centrifugal force applying member including a shaft member installed at a rotational center axis of the centrifugal force applying member, a first bearing rotatably supporting one end portion of the shaft member, and a second bearing rotatably supporting the other end portion of the shaft member, wherein the housing includes a lid member in which the first bearing is installed and a bottom member in which the second bearing is installed, and wherein the lid member and the bottom member are comprised of a resin material having a flexibility such that the housing is expandable in response to pressurized blood in the hollow body cavity, the method comprising the steps of:

arranging the housing, force applying member, and support mechanism along the rotational center axis into a preliminary assembly state;

compressing the lid member and the bottom member along respective outer circumferential walls, wherein the housing is warped by compressing the lid member and bottom member against the shaft member such that an interface between the outer circumferential walls is increased by a predetermined distance after the first and second bearings are in contact with the shaft member; and joining the lid member and the bottom member by affixing the outer circumferential walls at the interface during the compression.

2. The method of manufacturing a centrifugal pump according to claim 1 wherein when a separation distance between the first bearing and the second bearing after the assembling step is a separation distance Do, wherein the predetermined distance of increasing the outer wall interface corresponds to an unhindered separation distance $D_1$ between the first bearing and the second bearing that would otherwise result without resistance from the shaft member, and wherein the separation distance $D_1$ is equal to or less than 99% of the separation distance $D_0$.

3. The method of manufacturing a centrifugal pump according to claim 2:
wherein the separation distance $D_1$ is in a range from 97% to 99% of the separation distance $D_0$.

4. The method of manufacturing a centrifugal pump according to claim 2:
wherein each outer circumferential wall includes a deformable portion in which the lid member and the bottom member are individually deformed along the interface in response to the compression;
wherein the deformation is frozen by the joining step; and
wherein the unhindered separation distance $D_1$ is adjusted according to an extent of deformation of the deformable portion.

5. The method of manufacturing a centrifugal pump according to claim 1:
wherein affixing the outer circumferential walls in the joining step is comprised of welding by irradiating a spot in the interface between the lid member and the bottom member with laser light.

6. The method of manufacturing a centrifugal pump according to claim 5,
wherein each of the lid member and the bottom member has light-transmitting characteristics, and
wherein the method further comprises the step of interposing an optical absorption material at the interface to be irradiated with the laser light.

7. The method of manufacturing a centrifugal pump according to claim 5 wherein the laser light is realized by a semiconductor laser.

8. The method of manufacturing a centrifugal pump according to claim 5 wherein the deformable portions individually incline with respect to a rotational axis of the shaft member.

* * * * *